US011238568B2

(12) United States Patent
Grossinger et al.

(10) Patent No.: US 11,238,568 B2
(45) Date of Patent: *Feb. 1, 2022

(54) METHOD AND SYSTEM FOR RECONSTRUCTING OBSTRUCTED FACE PORTIONS FOR VIRTUAL REALITY ENVIRONMENT

(71) Applicant: Facebook Technologies, LLC, Menlo Park, CA (US)

(72) Inventors: Nadav Grossinger, Foster City, CA (US); Emil Alon, Pardes Hana (IL)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,918

(22) Filed: Feb. 4, 2020

(65) Prior Publication Data

US 2020/0175655 A1    Jun. 4, 2020

Related U.S. Application Data

(63) Continuation of application No. 16/562,893, filed on Sep. 6, 2019, now Pat. No. 10,593,025, which is a
(Continued)

(51) Int. Cl.
*G06T 5/00* (2006.01)
*G16B 45/00* (2019.01)
(Continued)

(52) U.S. Cl.
CPC .............. *G06T 5/005* (2013.01); *G02B 27/01* (2013.01); *G06T 15/205* (2013.01); *G06T 19/20* (2013.01);
(Continued)

(58) Field of Classification Search
CPC .... G02B 27/01; G02B 27/017; G06T 15/205; G06T 19/20; G06T 2200/04; G06T 2207/30201; G06T 5/005; G16B 45/00
See application file for complete search history.

(56) References Cited

U.S. PATENT DOCUMENTS

| 5,886,735 A * | 3/1999 | Bullister | H04N 7/142 |
| | | | 348/14.01 |
| 6,211,903 B1 * | 4/2001 | Bullister | H04N 7/142 |
| | | | 348/14.01 |

(Continued)

FOREIGN PATENT DOCUMENTS

| JP | H11/96366 A | 4/1999 |
| JP | 2000/307973 A | 11/2000 |

(Continued)

OTHER PUBLICATIONS

Canadian Intellectual Property Office, Office Action, Canadian Patent Application No. 2,956,508, dated Nov. 16, 2017, three pages.
(Continued)

*Primary Examiner* — Randolph I Chu
(74) *Attorney, Agent, or Firm* — Fenwick & West LLP

(57) ABSTRACT

A method and a system for reconstructing obstructed face portions are provided herein. The method may include the following steps: obtaining off-line 3D data, being 3D data of a head of a person not wearing a face-obstructing object, being an object which obstructs a portion of the face of the person; obtaining in real time, real-time 3D data, being 3D data of said head, wherein said person wears said face-obstructing object; applying a 3D transformation to at least a portion of the off-line 3D data, based on the real-time 3D data, to yield reconstructed real time 3D data, being real-time 3D data related to the obstructed face portions; and merging the reconstructed real time 3D data into the real-
(Continued)

time 3D data. The system may implement the aforementioned steps over a computer processor.

15 Claims, 8 Drawing Sheets

Related U.S. Application Data continuation of application No. 15/501,160, filed as application No. PCT/IL2015/050801 on Aug. 15, 2004, now Pat. No. 10,445,863.

(60) Provisional application No. 62/032,678, filed on Aug. 4, 2014.

(51) Int. Cl.
    *G06T 19/20*     (2011.01)
    *G02B 27/01*     (2006.01)
    *G06T 15/20*     (2011.01)

(52) U.S. Cl.
CPC ............ *G16B 45/00* (2019.02); *G02B 27/017* (2013.01); *G06T 2200/04* (2013.01); *G06T 2207/30201* (2013.01)

(56) References Cited

U.S. PATENT DOCUMENTS

| | | | |
|---|---|---|---|
| 7,139,767 B1* | 11/2006 | Taylor | G06F 16/50 |
| 8,573,866 B2* | 11/2013 | Bond | G02C 11/10 |
| | | | 396/420 |
| 2002/0080094 A1* | 6/2002 | Biocca | H04N 13/344 |
| | | | 345/8 |
| 2007/0177793 A1 | 8/2007 | Gu | |
| 2009/0003662 A1* | 1/2009 | Joseph | G06T 11/00 |
| | | | 382/118 |
| 2012/0327196 A1* | 12/2012 | Ohba | H04N 7/147 |
| | | | 348/49 |
| 2013/0009868 A1 | 1/2013 | Sako et al. | |
| 2013/0208234 A1 | 8/2013 | Lewis | |
| 2015/0212330 A1* | 7/2015 | Li | G02B 27/0172 |
| | | | 345/419 |
| 2015/0310263 A1* | 10/2015 | Zhang | G02B 27/0093 |
| | | | 382/103 |
| 2016/0217621 A1* | 7/2016 | Raghoebardajal | G06T 19/006 |

FOREIGN PATENT DOCUMENTS

| | | |
|---|---|---|
| JP | 2001/501346 A | 1/2001 |
| JP | 2010/206307 | 9/2010 |
| JP | 2013/175929 A | 9/2013 |
| RU | 2488882 C1 | 7/2013 |
| WO | WO-98/36631 | 2/1998 |

OTHER PUBLICATIONS

European Patent Office, European Search Report and Opinion, European Patent Application No. 15829328.2, dated Dec. 19, 2017, eleven pages.
Figueroa-Villanueva, Miguel A., et al. "Providing High Social Presence for Mobile Systems via an Unobtrusive Face Capture System." Proc. of Presence. 2005. (Year: 2005).
Frueh, Christian, Avneesh Sud, and Vivek Kwatra. "Headset removal for virtual and mixed reality." ACM SIGGRAPH 2017 Talks. ACM, 2017. (Year: 2017).
Japan Patent Office, Office Action, Japanese Patent Application No. 2017/506358, dated Jul. 30, 2019, 10 pages.
PCT International Search Report and Written Opinion, F'CT/IL2015/050801, dated Dec. 18, 2015, 7 Pages.
Romera-Paredes, B., "Facial Expression Tracking from Head-Mounted, Partially Observing Cameras," *Proceedings of the IEEE International Conference on Multimedia and Expo (ICME)*, Jul. 14, 2014, six pages.
Takemura, M. et al., "Diminishing Head-Mounted Display for Shared Mixed Reality," *Proceedings of the International Symposium on Mixed and Augmented Reality (ISMAR '02)*, 2002, IEEE Computer Society, Los Alamitos, California, USA, eight pages.
Takemura, M., "Eye-contact by means of human image processing for co-operative mixed reality environment," Unofficial Translation, The Institute of Electronics, Information and Communication Engineers, Japan, Technical Report, vol. 102, No. 554, Jan. 9, 2003, 11 pages.
Takemura, Masayuki, and Yuichi Ohta. "Generating High-Definition Facial Video for Shared Mixed Reality." MVA. 2005. (Year: 2005).
Indian Patent Office, Examination Report, Indian Patent Application No. 201747007530, dated Jul. 22, 2020, five pages.
Lee, E. C. et al. "Robust Gaze Tracking Method for Stereoscopic Virtual Reality Systems." Human-Computer Interaction. HCI Intelligent Multimodal Interaction Environments, HCI 2007, Lecture Notes in Computer Science, vol. 4552, Jul. 22, 2007, pp. 700-709.
European Patent Office, Summons to Attend Oral Proceedings, European Patent Application No. 15829328.2, dated Apr. 24, 2020, 13 pages.
International Preliminary Report on Patentability for Application No. PCT/IL2015/050801, dated Feb. 16, 2017, 7 pages.

\* cited by examiner

*800*

810 — OBTAINING OFF-LINE 3D DATA, BEING 3D DATA OF A HEAD OF A PERSON NOT WEARING A FACE-OBSTRUCTING OBJECT, BEING AN OBJECT WHICH OBSTRUCTS A PORTION OF THE FACE OF THE PERSON

820 — OBTAINING IN REAL TIME, REAL-TIME 3D DATA, BEING 3D DATA OF SAID HEAD, WHEREIN SAID PERSON WEARS SAID FACE-OBSTRUCTING OBJECT

830 — OBTAINING OBSTRUCTED PORTIONS DATA BEING DATA INDICATIVE OF FACE PORTIONS OBSTRUCTED BY THE FACE-OBSTRUCTING OBJECT, WHEREIN THE OBSTRUCTED PORTIONS DATA IS BASED AT LEAST PARTIALLY ON NON-OBSTRUCTED PORTIONS DERIVED FROM THE REAL-TIME 3D IMAGES

840 — APPLYING A 3D TRANSFORMATION TO AT LEAST A PORTION OF THE OFF-LINE 3D DATA, BASED ON THE REAL-TIME 3D DATA, TO YIELD RECONSTRUCTED REAL TIME 3D DATA, BEING REAL-TIME 3D DATA RELATED TO THE OBSTRUCTED FACE PORTIONS

850 — MERGING THE RECONSTRUCTED REAL TIME 3D DATA INTO THE REAL-TIME 3D DATA

Figure 8

METHOD AND SYSTEM FOR RECONSTRUCTING OBSTRUCTED FACE PORTIONS FOR VIRTUAL REALITY ENVIRONMENT

CROSS REFERENCE TO RELATED APPLICATIONS

This application is a continuation of co-pending U.S. application Ser. No. 16/562,893, filed Sep. 6, 2019, which is a continuation of U.S. application Ser. No. 15/501,160, filed Feb. 1, 2017, now U.S. Pat. No. 10,445,863, which was the National Stage of International Application No. PCT/IL15/50801, filed Aug. 4, 2015, which claims the benefit of U.S. Provisional Application No. 62/032,678, filed Aug. 4, 2014, each of which is incorporated by reference in its entirety.

FIELD OF THE INVENTION

The present invention relates generally to virtual reality environments, and more particularly, to such environments integrating real images of the virtual reality environment participants.

BACKGROUND

Prior to the background of the invention being set forth, it may be helpful to set forth definitions of certain terms that will be used hereinafter.

The term 'virtual reality' (VR) as used herein is defined as a computer-simulated environment that can simulate physical presence in places in the real world or imagined worlds. Virtual reality could recreate sensory experiences, including virtual taste, sight, smell, sound, touch, and the like.

The term 'virtual reality headset' as used herein is defined as a head mounted display (HMD) by which a 3D computer-simulated environment is projected stereoscopically into the eyes of the user, with each eye receiving a slightly different point of view of the computer-simulated environment. One such virtual reality headset known in the art is Oculus Rift™. The virtual reality headset may be implemented as any type of stereoscopic visor and may be held within a helmet-type structure.

The term '3D model' as used herein is defined as the product of 3D modeling being the process of developing a mathematical representation of any three-dimensional surface of object (either inanimate or living). The model can also be physically created e.g., using 3D printing devices or even manually. 3D models may represent a 3D object using a collection of points in 3D space, connected by various geometric entities such as triangles, lines, curved surfaces, etc. Being a collection of data (points and other information).

The term '3D data' as used herein is defined as any data structure, of any form and kind, derived from 3D objects. 3D data may include, for example, 3D models, 3D images but also less structured data types.

One challenge of 3D virtual reality today is to incorporate actual image or data of the users (e.g., virtual reality environment participants) for example in the view point of each of the other users in a seamless manner. As some of the virtual reality systems currently available require some form of virtual reality headsets within which the near eye display is being integrated, at least a portion of the face is being obstructed by the headset.

In some 3D virtual reality applications, it is desirable to capture in real time the image of the user and merge the image into the view of each of the other users. In such applications, a helmet such as a virtual reality headset or a face obstructing object serving as a near eye display may cause loss of data, for example portions the user's face, which undermines the altogether user experience.

FIG. 1 illustrates a virtual reality environment 100 according to the prior art, in which both persons (users) 106 and 108 are wearing a near eye display unit 102 and 104 respectively, which happen to obstruct at least a portion of their faces. Their respective views (what they see through the displays) 110 and 112 are usually 3D in nature and so each viewing image contains two viewpoints (not shown for simplicity). The views 110 and 112, presented to the users via their respective near eye displays include a computer-simulated environment not showing real objects 103 and 105. Views 110 and 112 of computer-simulated environment are adjusted in real-time responsive to the movements of the user. Views 110 and 112 present images of their counter participant 106A and 108A wearing the near eye display 102A and 104A which obstruct most of their faces in views 112 and 110. The face obstruction is an undesirable outcome and undermines the overall user experience.

SUMMARY

Some embodiments of the present invention overcome the aforementioned disadvantages of the prior art by providing a method and a system for reconstructing obstructed face portions for virtual reality environments. The method may include the following steps: obtaining off-line 3D data, being 3D data of a head of a person not wearing a face-obstructing object, being an object which obstructs a portion of the face of the person; obtaining in real time, real-time 3D data, being 3D data of said head, wherein said person wears said face-obstructing object; applying a 3D transformation to at least a portion of the off-line 3D data, based on the real-time 3D data, to yield reconstructed real time 3D data, being real-time 3D data related to the obstructed face portions; and merging the reconstructed real time 3D data into the real-time 3D data. The system may implement the aforementioned steps over a computer processor.

These, additional, and/or other aspects and/or advantages of the embodiments of the present invention are set forth in the detailed description which follows; possibly inferable from the detailed description; and/or learnable by practice of the embodiments of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 8 is a flowchart illustrating a method according to some embodiments of the present invention.

DETAILED DESCRIPTION

Figure 1:
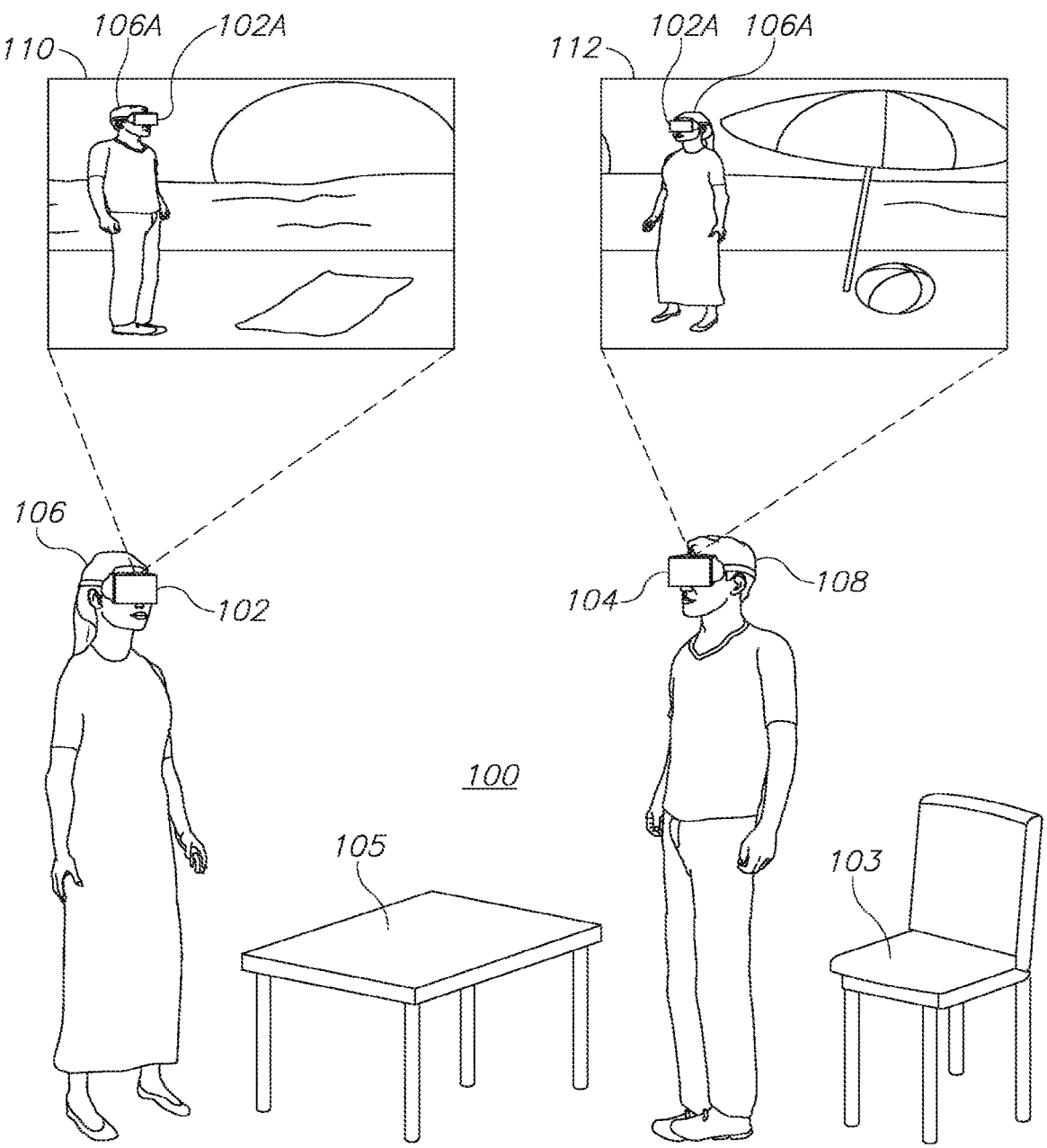
FIG. 1 is a schematic block diagram illustrating a virtual reality environment according to the prior art.

With specific reference now to the drawings in detail, it is stressed that the particulars shown are by way of example and for purposes of illustrative discussion of the preferred embodiments of the present technique only, and are presented in the cause of providing what is believed to be the most useful and readily understood description of the principles and conceptual aspects of the present technique. In this regard, no attempt is made to show structural details of the present technique in more detail than is necessary for a fundamental understanding of the present technique, the description taken with the drawings making apparent to those skilled in the art how the several forms of the invention may be embodied in practice.

Before at least one embodiment of the present technique is explained in detail, it is to be understood that the invention is not limited in its application to the details of construction and the arrangement of the components set forth in the following description or illustrated in the drawings. The present technique is applicable to other embodiments or of being practiced or carried out in various ways. Also, it is to be understood that the phraseology and terminology employed herein is for the purpose of description and should not be regarded as limiting.

Some embodiments of the present invention address the challenge of reconstructing a facial portion of a virtual reality participant in cases where a portion of the face is obstructed, usually by a 3D virtual reality headset such as Oculus Rift™ headset or Google Glass™.

Operating in the 3D virtual reality domain makes the solution specifically challenging in order to reconstruct a real-time 3D data such as 3D image of the virtual reality participant's face in a manner seamless to the other viewer-participants.

Figure 2:
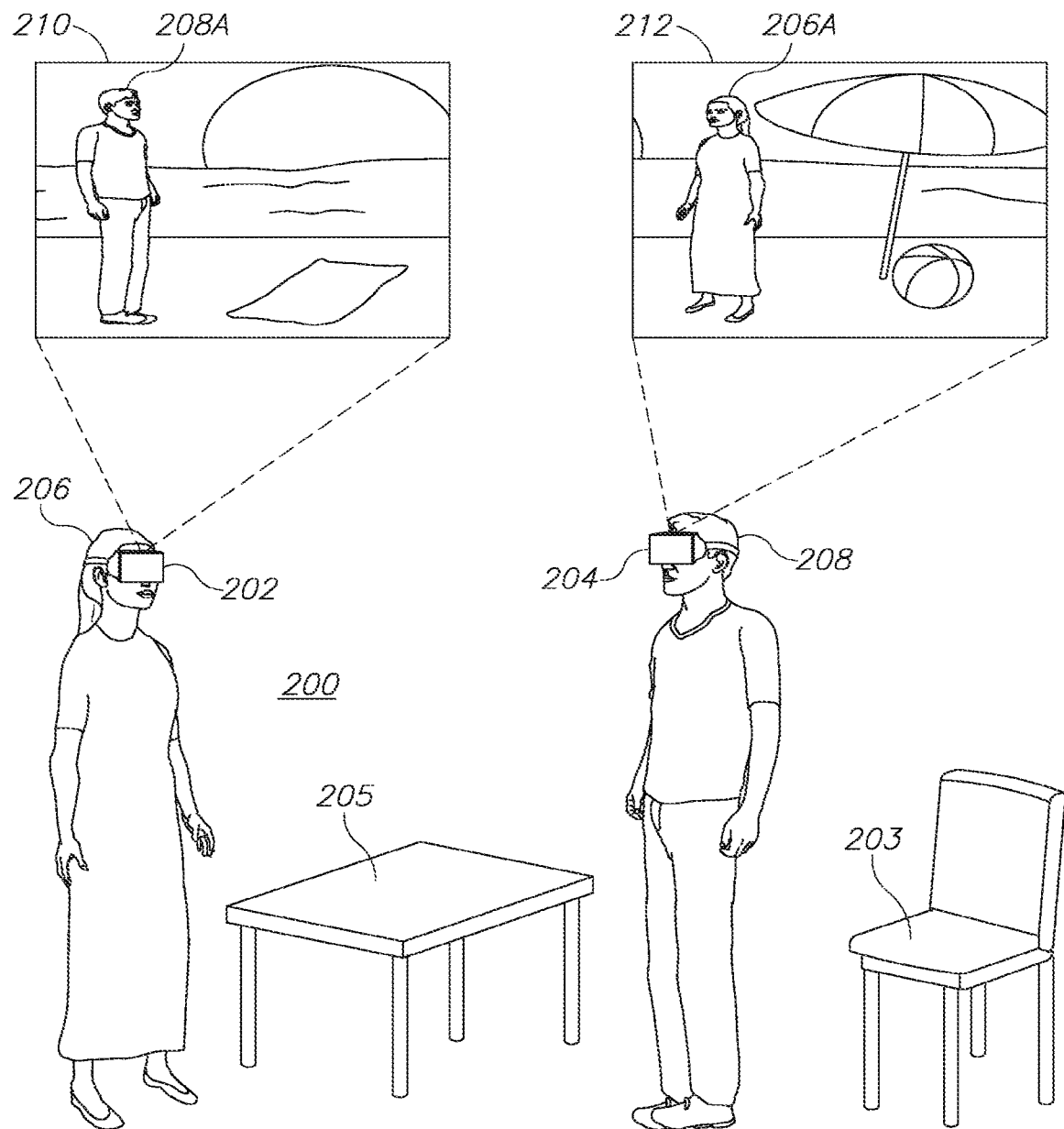
FIG. 2 is a schematic block diagram illustrating a virtual reality environment according to embodiments of the present invention.

FIG. 2 is a schematic block diagram illustrating a virtual reality environment according to embodiments of the present invention. A scene 200 in a virtual reality system is depicted, in which both persons (participants) 206 and 208 are wearing a near eye display or a VR headset 202 and 204 respectively, which happen to obstruct their faces. However, as opposed to FIG. 1, their respective views 210 and 212 which as presented via their near eye displays 202 and 204 show their counter participant not wearing the near eye display (real objects 203 and 205 are also not shown as the background of the real world is being replaced with a computer simulated environment). This is enabled by replacing part of the image that includes the obstructing object with a supplementary or modified face images that are being updated in real time, based on actual movements and/or expressions and/or gestures of the participants as will be explained in detail below.

Figure 3:
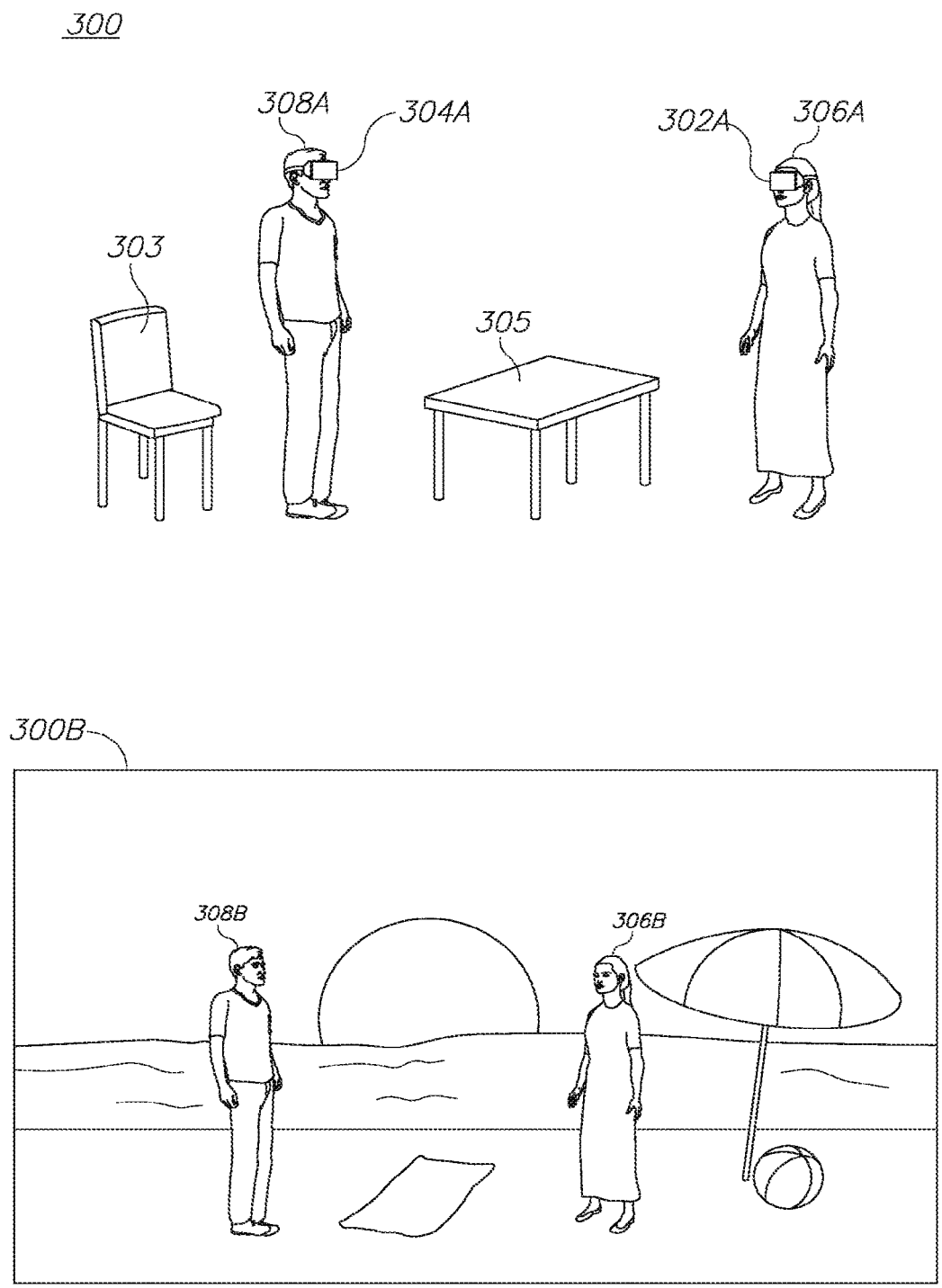
FIG. 3 is a schematic diagram illustrating a virtual reality environment according to embodiments of the present invention.

FIG. 3 is a schematic block diagram illustrating a virtual reality environment according to some embodiments of the present invention. Here, a third participant (not shown) is viewing two other participants 308A and 306A who wear helmets such as VR headsets 304A and 302A in the real world 300 which also contain real objects 303 and 305. In the virtual reality view 300B presented to the third user, the two other participants 308B and 306B are presented without the helmets as these were seamlessly replaced with reconstructed face images.

Figure 4:
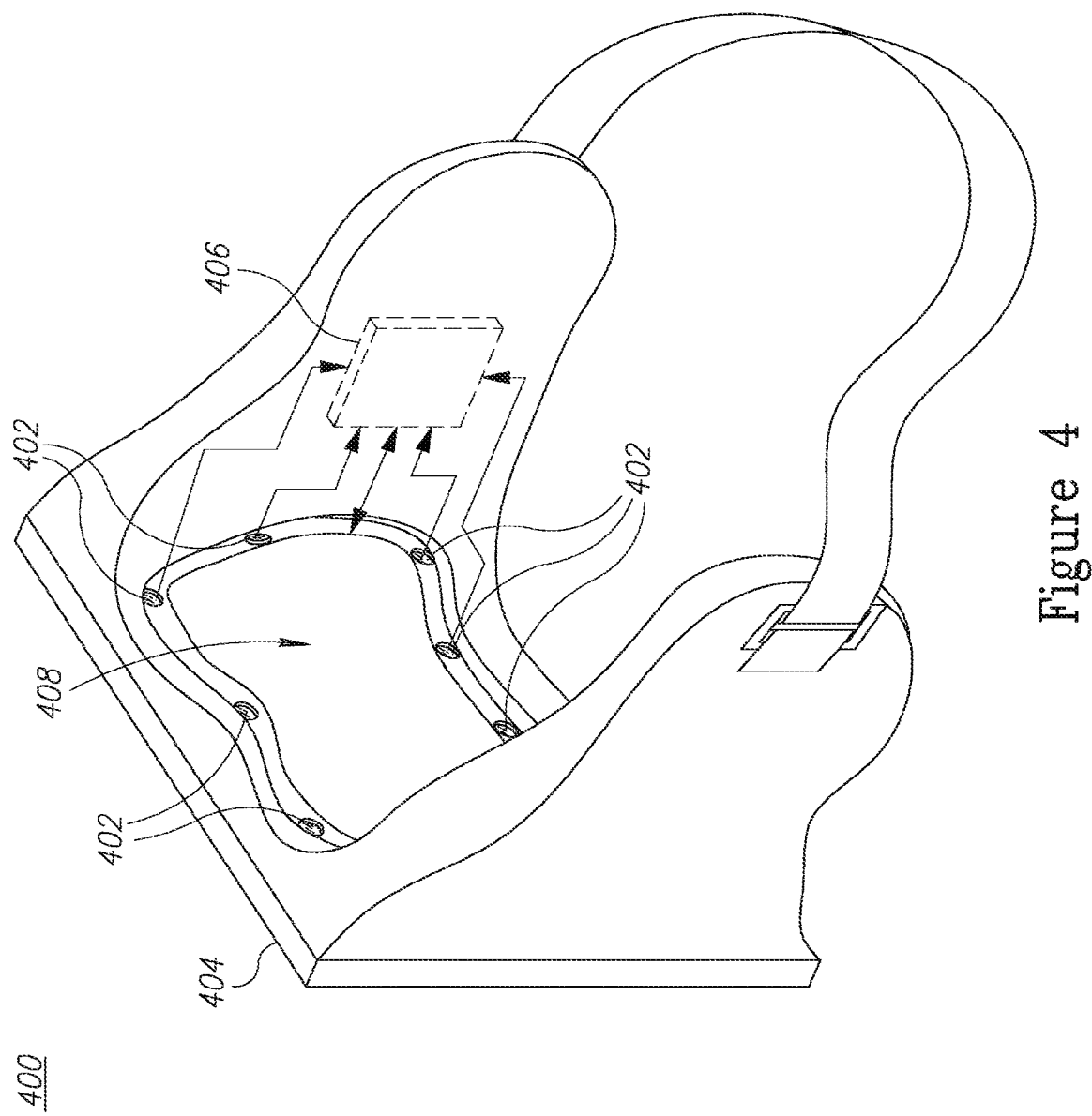
FIG. 4 is a schematic diagram illustrating a system in accordance with embodiments to the present invention.

FIG. 4 is a schematic diagram illustrating an aspect in accordance with some embodiments according to the present invention. A user helmet 404 such as a VR headset is shown with a plurality of sensors 402 along its inner side (attachable to the user's face). The sensors are configured to sense the user's gestures such as the eyes (e.g., pupil of the eye and eyelid movement) and a computer processor is configured to modify a base image of the face based on the ongoing gestures and present them in real time (or with as little latency possible). By way of illustration, sensors 402 may sense movements of the facial skin that are indicative of the user laughing or smiling. In response, the base image of his or her face will undergo a process of image processing applying the effect of the laugh or the smile such as stretching various portions. This process is being updated in real time. Consequently, other viewers will be presented with the modified smiling face image of the user which will be seamlessly inserted into the image of the user, instead of the obstructed portion of the face.

Figure 5:
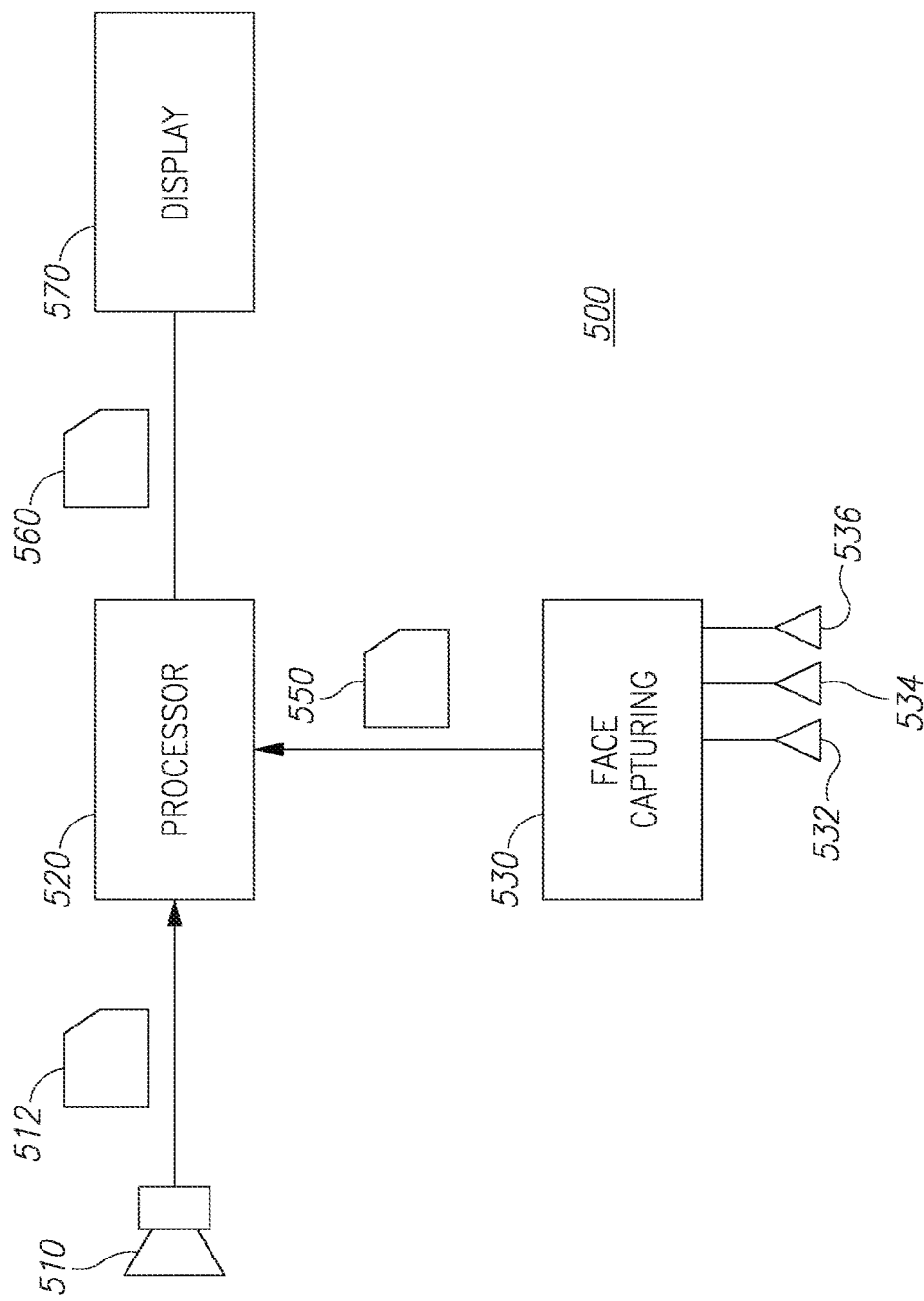
FIG. 5 is a schematic block diagram illustrating a system in accordance with embodiments according to the present invention.

FIG. 5 is a schematic block diagram illustrating a system 500 in accordance with embodiments according to the present invention. System 500 may include: a 3D data capturing device 510 configured to capture a 3D data (e.g., image) 512 of a scene containing at least one person wearing a face-obstructing object, wherein the capturing is taken from a view point of a specified user. System 500 may further include a computer processor 520 configured to: obtain data 550 indicative of, for example, face portions obstructed by the face-obstructing object, possibly from a face capturing module 530 which in turn receives the data from sensors 532-534 or other sources such as networked databases. A possible source for 2D images of users faces may be social networks such as add Facebook™ or LinkedIn™ which may store profile images of users. These 2D images may be used for generating 3D data of the head or the face of the user.

Computer processor 520 may be further configured to reconstruct 3D data of the (e.g., an image) of the obstructed face portions based on the obtained data. Computer processor 520 may be further configured to merge the reconstructed face image into respective location at the captured image of the scene. System 500 may further include a near eye display 570 configured to present the merged image to the specified user, wherein the merged image is placed into a computer-simulated environment adjustable based on the view point of the specified user.

According to some embodiments of the present invention, the face-obstructing object comprises one or more sensors located on an inner side of said face-obstructing object, wherein the sensors are configured to carry out the obtaining data indicative of face portions obstructed by the face-obstructing object.

According to some embodiments of the present invention, the sensing by the sensors may be in the form of image capturing and wherein said obtained data is an image of portions of the obstructed face.

According to some embodiments of the present invention, the sensors may be configured to sense facial gestures, and wherein the reconstructing of a face image is carried out by modeling sensed gestures to change the face relative to a base image of the obstructed face portions captured previously.

According to some embodiments of the present invention, computer processor 520 may be configured to obtain the data indicative of face portions obstructed by the face-obstructing object comprises obtaining a base image of the obstructed face portions, which has been previously captured.

According to some embodiments of the present invention, the obtaining of a base image of the obstructed face portions, by the processor is carried out via searching on networked databases.

According to some embodiments of the present invention, the reconstructing of a face image of the obstructed face portions may be based on an obtained data which is carried out by the processor by monitoring at least one of: position, orientation, profile, and vital signs (e.g., heart beat rate, respiratory system indicators etc.) of the at least one person wearing the a face-obstructing object, and applying the obtained data onto a three dimensional model of the face of the at least one person, to yield a modified face image.

According to some embodiments of the present invention, the face-obstructing object comprises a near eye display.

According to some embodiments of the present invention, the near eye display is incorporated within a helmet.

According to some embodiments of the present invention, the computer-simulated environment may be a three dimensional scene common to the specified user and the at least one person wearing the face-obstructing object.

Figure 6:
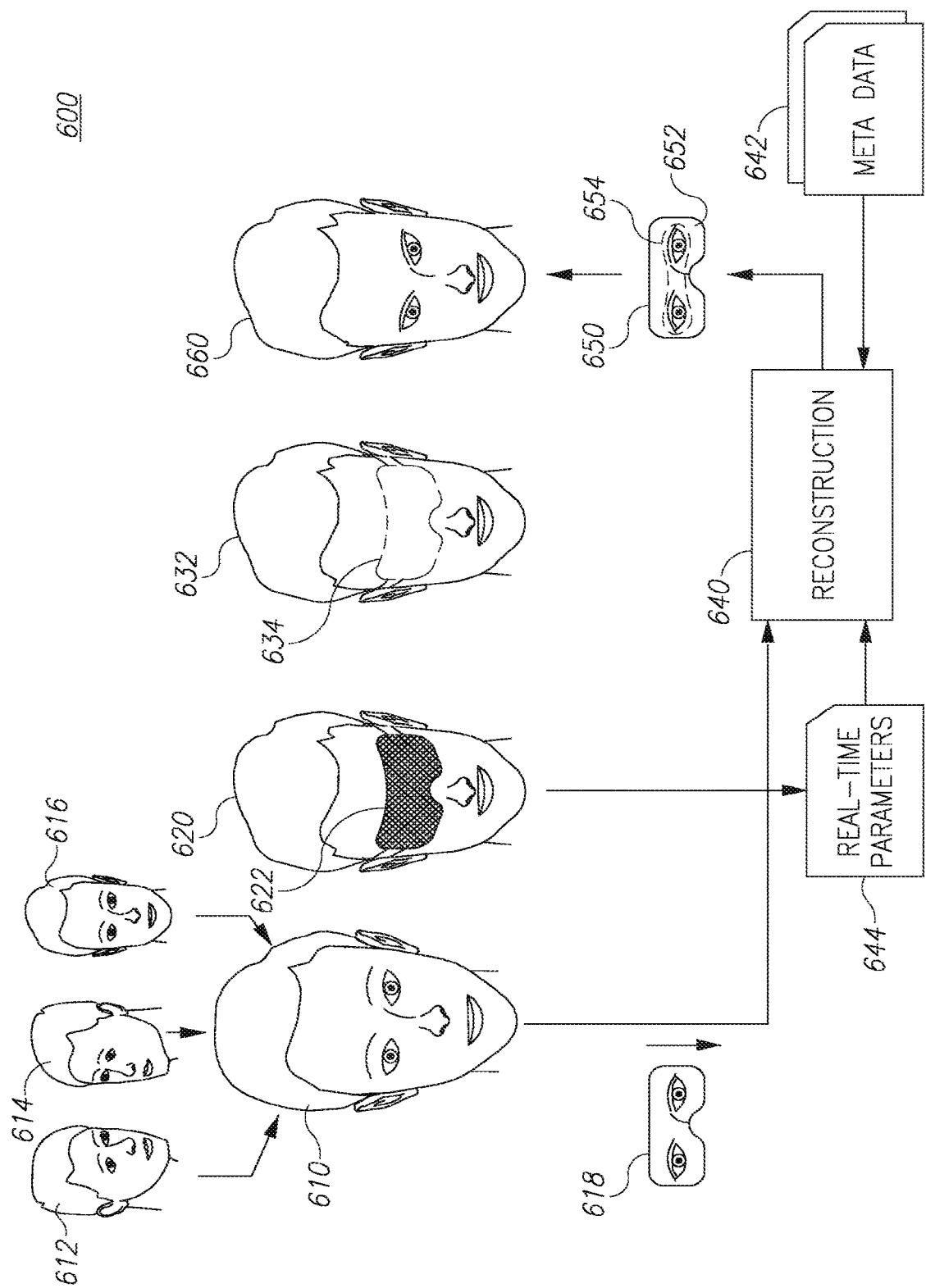
FIG. 6 is a schematic diagram illustrating a sequence of actions taken in accordance with embodiments of the present invention.

FIG. 6 is a schematic diagram 600 illustrating a sequence of actions taken in accordance with embodiments of the present invention. In a first step, off-line 3D data (e.g., in the form of a 3D model) of the head of a person 610 is being obtained, possibly but not exclusively based on a plurality of 2D images of the person 612, 614, and 616. 2D images of the person 612, 614, and 616 may be captured in an off-line session prior to wearing the helmet or may be obtained from third party sources such as networked databases.

Alternatively, the off-line 3D data may be obtained using structured light technology, prior to wearing the virtual reality headgear. Specifically, by using structured light, such as disclosed in WIPO PCT Application Publication No. WO2013088442, which is incorporated herein by reference in its entirety, a depth map of the head or face of the user may be generated from which the off-line 3D data may be retrieved.

Then, in a second step, real-time 3D data (e.g., model) of the user 620 is obtained, while the person is wearing a face obstructing object 622 (e.g., the virtual reality headset) the real-time image is being constantly updated. In a third step a 3D transformation may be applied in a reconstruction module 640 to off-line 3D data 610 or a portion of it 618 (which corresponds with the borders of the obstructed portions 634 which may be segmented out from 3D model 632). The 3D transformation may be based on real-time 3D data (model) 620 and more specifically, real-time parameters 644 from which the appearance of obstructed portions 634 may be estimated.

Real-time parameters 644 may include, for example: position and orientation of the user's face, or expressions, but also how tired the person is, and what type of emotions are being experienced in real time. These real-time parameters 644 are all being used in order to estimate and reconstruct the face portions that are being obstructed by the virtual reality headset The product of the reconstruction module (or step) is a reconstructed real-time data (or model) 650 which includes a sub portion of area that is affected by non-obscured portions 652, usually the inner cheeks affected by changes of gestures made to the outer cheeks. The appearance of this area may be estimated based on real-time parameters 644 relating to the non-obstructed portions. Another area is the area that is not affected by non-obstructed portions 654 (e.g., the eyes). The appearance of the eyes may be estimated based on another model, and using meta data 642 from sources external to real-time 2D data 622 such as which direction the person is looking at, given that in the virtual reality environment the person is interacting with another person (whose position is also known). Finally, reconstructed real-time 3D data (or model) 650 may be merged into real-time 3D data (or model) possibly with the obstructed portions segmented out 632, to yield a reconstructed real-time 3D data (or model) of the head of the person, with the obstructed portions reconstructed. Model 660 may then be generated into a 3D image to be presented to the other person(s) participating in the virtual reality environment.

Figure 7:
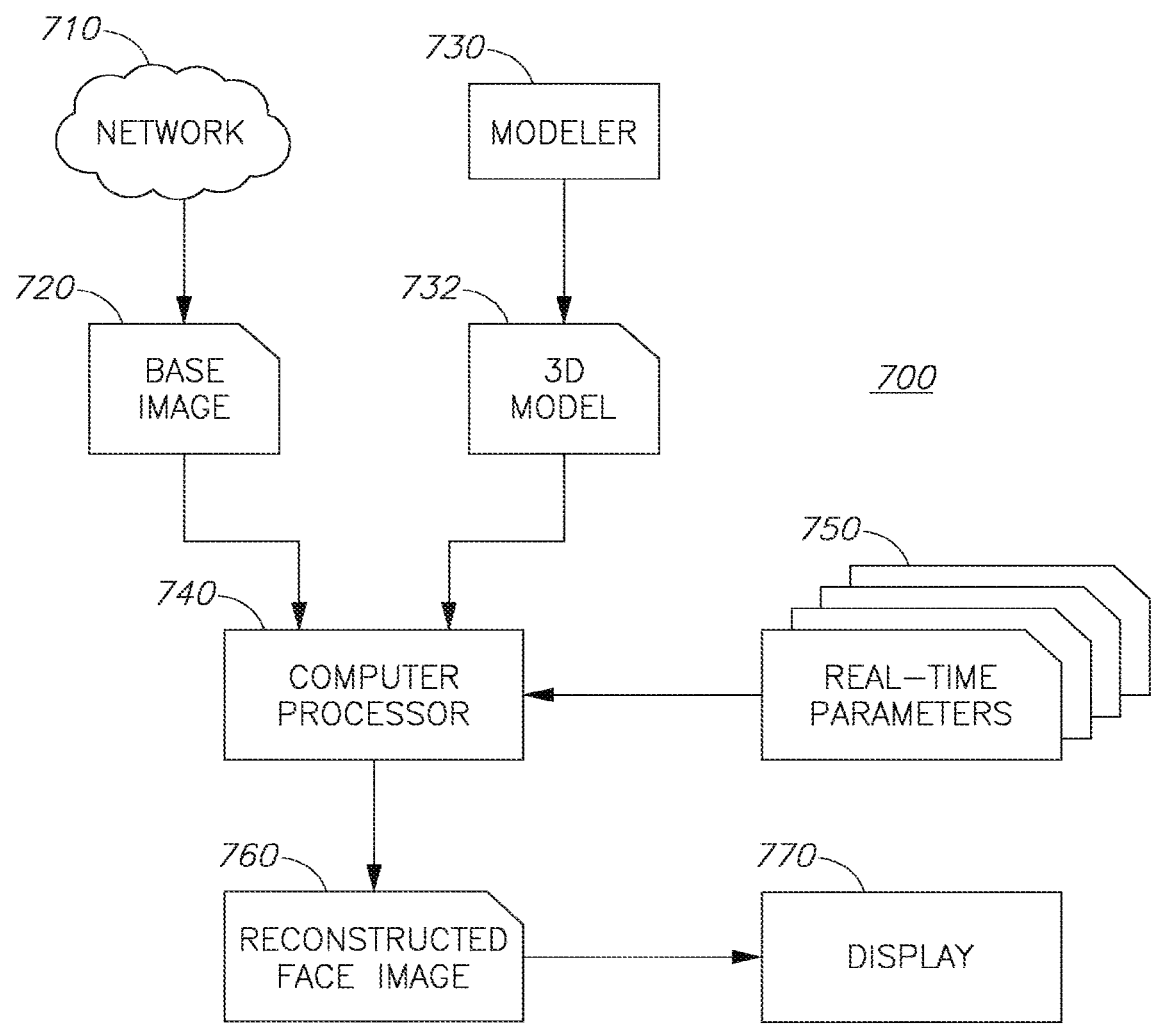
FIG. 7 is a schematic block diagram illustrating an aspect of a system in accordance with embodiments according to the present invention.

FIG. 7 is a schematic block diagram illustrating an aspect of a system in accordance with embodiments according to the present invention. Specifically, a schematic illustration explaining how the obstructed face portion may be reconstructed is presented herein. System 700 may include a network 710 which may be the Internet serving as a source for face images of participants. As indicated above, these base images 720 are usually raw images which may be harvested from social network websites such as Facebook™.

Concurrently, a modeler 730 being implemented by software may generate a 3D model 732 of the face that need to be reconstructed. The model may be based on several 2D views of the head of the person whose face image need to be reconstructed. Then, both the base image 720 of the face retrieved form the third party source and the 3D model 732 are fed into a computer processor 740 which processes them, together with real-time parameters 750 relating to the actual position and orientation and perhaps facial gestures, of the head of the participant whose face image needs to be reconstructed. The output of computer processor 740 is a reconstructed face image 760 in which the actual position, nearby environment and orientation of the participant are used in order to adjust the base image and to apply on the model so that the reconstructed face image will be presented in the virtual reality view as natural as possible. Examples for real time parameters may be direction of view of the participant, his or her physical condition such as how tired he or she is which may affect their eye positions and general appearance of their face and the like, their current mood e.g. happy/angry/sad etc., their nearby environment e.g. at home or outside on the beach in a hot weather. This appearance-affecting data may be used by the modeler to reconstruct and modify the base image, by methods known in the art (e.g., of texturing and digital animation).

In some other embodiments, facial expressions may be deduced by the context of the virtual reality environment such as what has occurred to the user in the virtual world (e.g. in a game) and so the reconstructed face image can be dynamically adjusted based on the virtual world activities.

FIG. 8 is a high level flowchart illustrating a method 800 according to some embodiments of the present invention. It is understood that method 800 may be implemented by an architecture that is different from the aforementioned architecture of system 500. Method 800 may include: obtaining off-line 3D data, being 3D data of a head of a person not wearing a face-obstructing object, being an object which obstructs a portion of the face of the person 810; obtaining in real time, real-time 3D data, being 3D data of said head, wherein said person wears said face-obstructing object 820; applying a 3D transformation to at least a portion of the off-line 3D data, based on the real-time 3D data, to yield reconstructed real time 3D data, being real-time 3D data related to the obstructed face portions 830; and merging the reconstructed real time 3D data into the real-time 3D data 840.

According to some embodiments of the present invention, the off-line 3D data may be an off-line 3D model and the real-time 3D data may be a real-time 3D model. A model can be any mathematical or real structure indicative of spatial characterization.

According to some embodiments of the present invention, the method may further include the step of generating a merged real-time 3D image from the merged reconstructed real time 3D data and the real-time 3D data.

According to some embodiments of the present invention, the real-time 3D data may be super-positioned over a virtual reality (VR) environment.

According to some embodiments of the present invention, the real-time 3D data may be obtained by monitoring at least one of: position, orientation, profile, and vital signs of the person wearing the face-obstructing object.

According to some embodiments of the present invention, the method may further include the step of applying the obtained real-time 3D data onto a 3D model of the face of said person, to yield a modified face image.

According to some embodiments of the present invention, the 3D transformation may further include using data obtained from non-obstructed face portions of the person for estimating obstructed face portions that are affected by changes to the non-obstructed face portions. Specifically, the estimating may be carried out based on sensing facial expression from the real-time 3D data.

According to some embodiments of the present invention, the 3D transformation may further include estimating an appearance of obstructed portions that are unaffected by changes to the non-obstructed face portions (e.g., the eyes) and using the estimation in the 3D transformation. Specifically, the estimating may be carried out based on meta-data relating to said person.

According to some embodiments of the present invention, the obstructed portions of the at least one person may be at least partially reconstructed based on occurrences in the VR environment. It is understood that this feature may also be implemented to the non-obstructed portions of the face.

According to some embodiments of the present invention, the obtaining of the off-line 3D data may be carried out via an external database that may store 2D images received from a computer network. Alternatively obtaining of the off-line 3D data may be carried out via a 3D sensor, prior to beginning a session of the VR environment.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not to be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method comprising:

sensing, by a sensor on an inner side of a face-obstructing object, facial gestures of face portions of a person obstructed by the face-obstructing object; and reconstructing a 3D face image of the obstructed face portions by modeling the sensed facial gestures to change the obstructed face portions relative to a previously captured base image of the obstructed face portions of the person.

2. The method according to claim 1, further comprising presenting the reconstructed 3D face image to a viewing user via a display.

3. The method of claim 1, further comprising capturing an image of a scene containing the person wearing the face-obstructing object.

4. The method according to claim 1, wherein the base image of the obstructed face portions further comprises unobstructed face portions of the person.

5. The method according to claim 1, further comprising retrieving the base image from a social network.

6. The method according to claim 5, further comprising modifying the base image based on an environmental condition affecting the person.

7. The method according to claim 1, wherein the reconstructing the 3D face image comprises monitoring at least one of: position, orientation, or profile; and applying the obtained data onto a three dimensional model of the face of the person to yield a modified face image.

8. The method according to claim 1, wherein the reconstructing the 3D face image comprises monitoring vital signs of the at least one person wearing the face-obstructing object, and applying the obtained data onto a three dimensional model of the face of the at least one person, to yield a modified face image.

9. A system comprising:
a computer processor configured to:
obtain, from a sensor on an inner side of a face-obstructing object, sensed facial gestures of face portions of a person obstructed by the face-obstructing object; and
reconstruct a 3D face image of the obstructed face portions by modeling the sensed facial gestures to change the obstructed face portions relative to a previously captured base image of the obstructed face portions of the person.

10. The system according to claim 9, further comprising a display configured to present the reconstructed 3D face image.

11. The system according to claim 9, further comprising an image capturing device configured to capture an image of a scene containing the person wearing the face-obstructing object.

12. The system according to claim 9, wherein the base image of the obstructed face portions further comprises unobstructed face portions of the person.

13. The system according to claim 9, wherein the computer processor is further configured to retrieve the base image from a social network.

14. The system according to claim 13, wherein the computer processor is further configured to modify the base image based on an environmental condition affecting the person.

15. A computer program product comprising a non-transitory computer-readable storage medium containing computer program code for:
sensing, by a sensor on an inner side of a face-obstructing object, facial gestures of face portions of a person obstructed by the face-obstructing object; and
reconstructing a 3D face image of the obstructed face portions by modeling the sensed facial gestures to change the obstructed face portions relative to a previously captured base image of the obstructed face portions of the person.

\* \* \* \* \*